(12) United States Patent
Arpin

(10) Patent No.: US 9,701,128 B2
(45) Date of Patent: Jul. 11, 2017

(54) DEVICE FOR MEASURING A LEVEL IN A TANK

(71) Applicant: Dover Europe Sàrl, Vernier (CH)

(72) Inventor: Jean-Pierre Arpin, Beaumont-Monteux (FR)

(73) Assignee: DOVER EUROPE SÀRL, Vernier (CH)

( * ) Notice: Subject to any disclaimer, the term of this patent is extended or adjusted under 35 U.S.C. 154(b) by 0 days.

(21) Appl. No.: 14/919,156

(22) Filed: Oct. 21, 2015

(65) Prior Publication Data

US 2016/0114590 A1    Apr. 28, 2016

(30) Foreign Application Priority Data

Oct. 22, 2014 (FR) .................................. 14 60138

(51) Int. Cl.
| | | |
|---|---|---|
| *B41J 2/175* | (2006.01) | |
| *G01F 23/26* | (2006.01) | |
| *G01N 27/06* | (2006.01) | |

(52) U.S. Cl.
CPC ........... *B41J 2/17566* (2013.01); *B41J 2/175* (2013.01); *G01F 23/263* (2013.01); *G01F 23/268* (2013.01); *G01N 27/06* (2013.01); *B41J 2002/17579* (2013.01); *G01F 23/266* (2013.01)

(58) Field of Classification Search
CPC .................. G01F 23/24; B41J 2002/17579
See application file for complete search history.

(56) References Cited

U.S. PATENT DOCUMENTS

| | | | |
|---|---|---|---|
| 4,196,625 A | 4/1980 | Kern | |
| 4,483,463 A | 11/1984 | Buschmann | |
| 4,626,874 A | 12/1986 | Murai et al. | |
| 4,700,754 A | 10/1987 | Kringe | |
| 5,447,056 A * | 9/1995 | Foote .................. | G01F 23/24 |
| | | | 73/304 R |
| 5,546,005 A | 8/1996 | Rauchwerger | |

(Continued)

FOREIGN PATENT DOCUMENTS

| | | |
|---|---|---|
| EP | 0 028 399 A2 | 5/1981 |
| EP | 0 208 377 A1 | 1/1987 |

(Continued)

OTHER PUBLICATIONS

Written Opinion and Search Report issued in Application No. EP 15190721 dated Jan. 29, 2016.

(Continued)

*Primary Examiner* — Shelby Fidler
(74) *Attorney, Agent, or Firm* — Pearne & Gordon, LLP

(57) ABSTRACT

A device for continuously measuring a level of an ink in a tank (10) of a continuous ink-jet (CIJ) printer, including: a first pair of electrodes (24, 26) and part for connecting this pair of electrodes in series, for measuring the impedance of a first predetermined height of the ink, in the tank, a second pair of electrodes (16, 18) and part for connecting this second pair of electrodes in series, for measuring a second height of the ink in the tank, this second height being included between this first height and a maximum level; part for calculating the second height, from the resistive components of the 2 impedances measured, independently of the ink conductivity.

22 Claims, 14 Drawing Sheets

(56) References Cited

U.S. PATENT DOCUMENTS

| | | | |
|---|---|---|---|
| 2003/0010117 A1* | 1/2003 | Shon | G01F 23/24 73/304 R |
| 2005/0156962 A1* | 7/2005 | Sasaki | G01F 23/268 347/7 |
| 2007/0068249 A1 | 3/2007 | Eguchi | |
| 2007/0076023 A1* | 4/2007 | Knierim | B41J 2/17566 347/7 |
| 2009/0103904 A1* | 4/2009 | Wolff | G01F 23/242 392/402 |
| 2010/0077854 A1* | 4/2010 | Knierim | B41J 2/17513 73/304 R |
| 2014/0375321 A1* | 12/2014 | Ikeya | G01N 27/221 324/324 |

FOREIGN PATENT DOCUMENTS

| | | |
|---|---|---|
| EP | 0 784 784 A1 | 7/1997 |
| EP | 1 125 748 A1 | 8/2001 |
| EP | 1 493 586 A1 | 1/2005 |
| FR | 2 514 498 A1 | 4/1983 |
| JP | 59003319 A * | 1/1984 ............ G01F 23/24 |
| WO | 96/11385 A1 | 4/1996 |
| WO | 98/02718 A1 | 1/1998 |
| WO | 2008/062146 A1 | 5/2008 |
| WO | 2011/076810 A1 | 6/2011 |

OTHER PUBLICATIONS

Search Report issued in French Patent Application No. FR 15 60579 dated Sep. 6, 2016.
Machine Translation of European Patent Publication No. 1203934 dated May 8, 2002.
Machine Translation of International Publication No. 98/02718 dated Jan. 22, 1998.
Machine Translation of French Patent Publication No. 1436080 dated Apr. 22, 1966.
Gabriel Nicolae Popa et al., "A Study About a Resistive Stepped Transducer used for Water Level Measurement" Annals of the Faculty of Engineering Hundedoara—Journal of Engineering, vol. 7, No. 3, 2009.
Search Report issued in French Patent Application No. FR 14 60138 dated Jun. 19, 2015.

* cited by examiner

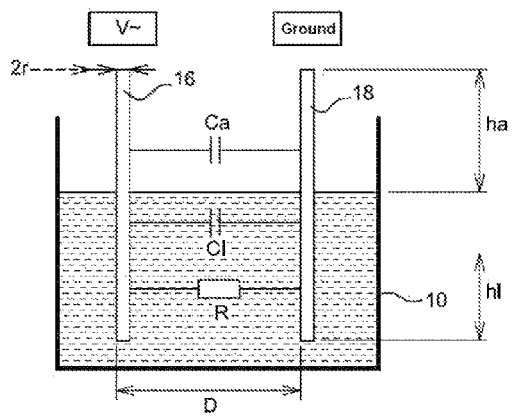
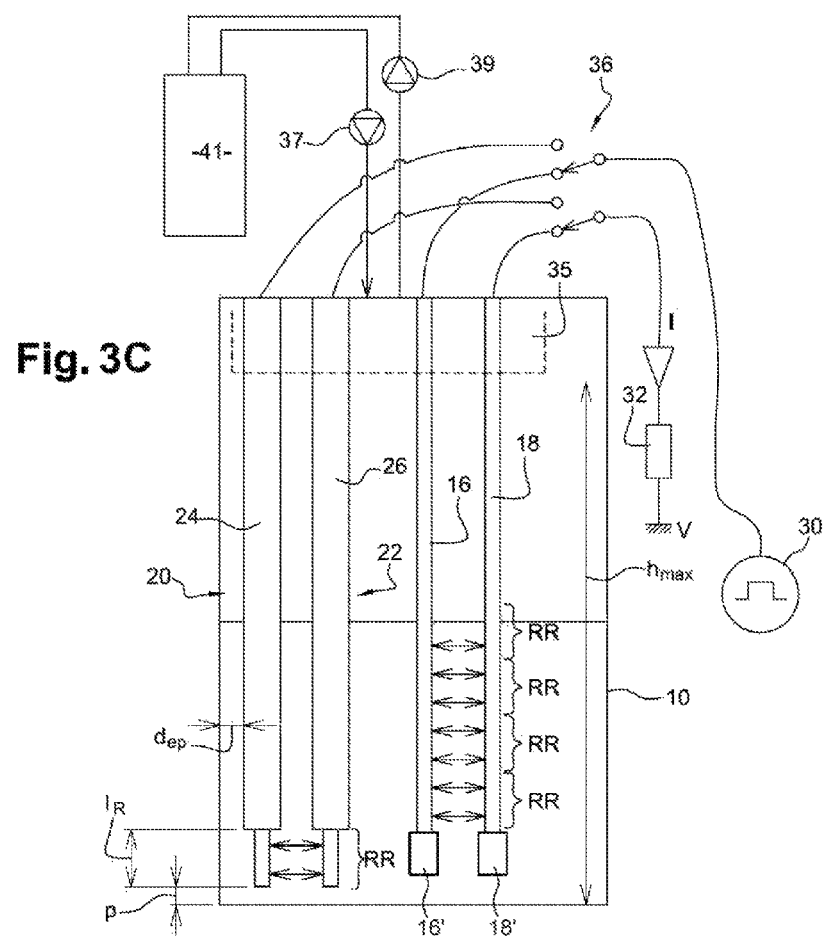

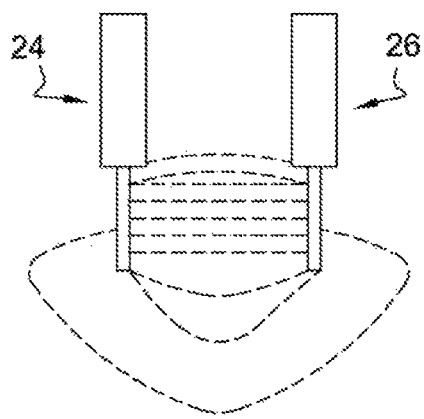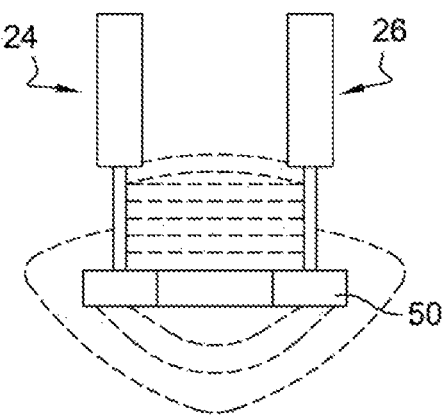
Fig. 8A    Fig. 8B
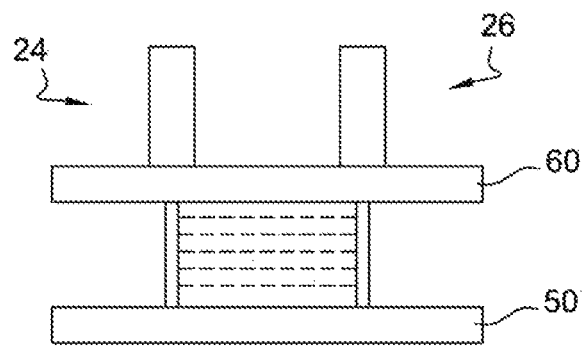
Fig. 8C

DEVICE FOR MEASURING A LEVEL IN A TANK

TECHNICAL FIELD AND PRIOR ART

The invention relates to the field of continuous ink jet (CIJ) printers.

It also relates to a device and a method for measuring a level of a conducting liquid, in particular ink in a tank of such a printer.

Continuous ink jet (CIJ) printers are well known in the field of industrial coding and labelling for various products, for example to label bar-codes, expiration date on food products, or even references or distance marks on cables or pipes directly on the production line and at a high rate. This kind of printer is also found in some fields of decoration where the graphic printing possibilities of the technology are exploited.

These printers have several standard sub-assemblies as shown in FIG. 1.

First, a printing head 1, generally offset from the body of the printer 3, is connected thereto by a flexible umbilical 2 joining the hydraulic and electrical connections required for operating the head by imparting it a flexibility which facilitates integration on the production line.

The body of the printer 3 (also called a console or cabinet) usually contains three sub-assemblies:
- an ink circuit at the bottom of the console (zone 4'), which enables, on the one hand, ink to be provided to the head at a stable pressure and with a suitable quality, and, on the other hand, the jet ink not used for printing to be dealt with;
- a controller located at the top of the console (zone 5'), capable of managing the action sequencing and performing processes enabling different functions of the ink circuit and of the head to be activated,
- an interface 6 which gives the operator means for implementing the printer and to be informed about its operation.

In other words, the cabinet includes 2 sub-assemblies: at the top portion, the electronics, the electric supply, and the operator interface, and at the bottom, an ink circuit providing ink, with a rated quality, under pressure to the head and the trough for recovering ink not used by the head.

FIG. 2 schematically represents a printing head 1 of a CIJ printer. It includes a drop generator 60 fed with electrically conducting ink, pressurised by the ink circuit.

This generator is capable of emitting at least one continuous jet through a small dimension port called a nozzle. The jet is transformed into a regular succession of drops having an identical size under the action of a periodical stimulation system (not represented) located upstream of the nozzle outlet. When the drops 7 are not for printing, they are directed to a gutter 62 which recovers them in order to recycle unused ink and to bring them back into the ink circuit. Devices 61 placed along the jet (charging and deflection electrodes) enable, by a command, the drops to be electrically charged and deflected in an electric field Ed. Consequently, they are deviated from their natural trajectory of ejection from the drop generator. The drops 9 for printing avoid the getter and will be deposited on the medium to be printed 8.

This description can be applied to so-called binary or multi-deflected continuous jet versions of continuous ink jet (CIJ) printers. The binary CIJ printers are equipped with a head the drop generator of which has a multitude of jets, each drop of a jet can only be oriented to 2 trajectories: printing or recovery. In multi-deflected continuous jet printers, each drop of a single jet (or of some spaced jets) can be deflected to various trajectories corresponding to charging commands being different from one drop to the other, thus making a sweeping of the zone to be printed along a direction which is the deflection direction, the other sweeping direction of the zone to be printed is covered by relatively displacing the printing head and the medium to be printed 8. Generally, the elements are arranged such that these 2 directions are substantially perpendicular.

An ink circuit of a continuous ink jet printer enables, on the one hand, ink under a controlled pressure, and possibly solvent, to be provided to the drop generator of the head 1 and, on the other hand, a depression to be created to recover unused fluids for printing and which then come back from the head.

It also enables consumables (ink and solvent delivery from a reservoir) to be managed and ink quality (viscosity/concentration) to be controlled and maintained.

Finally, other functions are related to the user comfort and the automatic takeover of some maintenance operations in order to ensure a constant operation regardless of the conditions of use. Among these functions, there are the solvent rinsing of the head (drop generator, nozzle, getter), preventive maintenance head, for example replacement of components having a limited lifetime, in particular filters, and/or pumps.

These different functions have very different purposes and technical requirements. They are activated and sequenced by the printer controller which will be all the more complex that the number and sophistication of the functions are great.

Generally, the ink circuit of known ink jet printers able to project inks remains an expensive element, because of the numerous hydraulic components to implement.

Therefore, the problem arises of making all or part of the functions of an ink circuit, in a CIJ type printer, at a lesser cost with a reduced number of components, while ensuring a minimum reliability or, in any case, a reliability expected by users, in particular related to the ink homogeneity throughout the consumption. It is thus attempted to implement as simple as possible components, in particular for functions such as level measurement in tanks, control and maintenance of ink quality. The latter can be defined in terms of ink viscosity and/or concentration.

As regards level sensors, sensors which measure one or more levels, yet discretely, are known. This sensor type can operate based on a capacitive or optical measurement, or with floaters which are triggered relative to a threshold. This type of device only enables a single or several discrete levels to be indicated: full, empty, low, intermediate.

For example, a known sensor implements level rods which indicate the presence or absence of current between the rods, this current being related to the ink level. Since it is not attempted to measure the value of this current, they are independent of the conductivity.

Document EP 0784784 describes such a discrete sensor.

Document WO 2011/076810 describes a continuous sensor, yet complex and expensive.

A system allowing for a continuous measurement has a dependency on the measuring medium. Therefore, either this medium has to be driven, or the variations have to be measured to provide necessary corrections. The signal produced by a resistive sensor will depend on ink conductivity, the one of a capacity sensor depends on the capacitance; a pressure sensor can be sensitive to the density and atmospheric pressure. For an acoustic sensor, the signal level will depend on the propagation speed in the medium measured.

Thus, the problem arises to find a new continuous type sensor, the measurement data it provides being independent of the measuring medium and in particular independent of the conductivity of the liquid the level of which is measured.

Preferably, such a sensor is easy to implement, and cheap.

DISCLOSURE OF THE INVENTION

The invention first relates to a device for continuously measuring a level in a tank of a continuous ink jet (CIJ) printer, including:
- first means for measuring the impedance of a first predetermined liquid height, in said tank;
- second means for measuring the impedance of any second height of the same liquid in said tank, in particular above said first height;
- means for estimating or calculating said second height, from, or based on, said 2 measured impedances, preferably the resistive components of said impedances.

Said first means may comprise a first pair of rods or electrodes and means for connecting this pair of electrodes in series, for measuring the impedance of a first predetermined height of the ink, in said tank.

Said second means may comprise a second pair of rods or electrodes and means for connecting this second pair of electrodes in series, for measuring the impedance of a second height of the ink in said tank, this second height being higher than said first height, for example being included between said first height and a maximum level.

A device according to the invention allows a continuous and linear measurement, independent of the conductivity of the liquid. This enables a specific calibration to be avoided for each liquid, or each ink, or even each printer.

Means, for example of the multiplexing means type, can be provided to allow alternatively measurements using said first means, or said first pair of electrodes, and said second means, or said second pair of electrodes. According to one embodiment, the first means for measuring the impedance of a first predetermined liquid height, in said tank, include two measuring rods or electrodes, intended to be mounted parallel in said tank, each including a measuring end of a conducting material, for measuring an impedance which corresponds to the first predetermined liquid height, and which remains constant for any second height higher than the first height.

The second means for measuring the impedance of any second liquid height, in said tank, can include two measuring rods or electrodes, each of a conducting material, intended to be mounted parallel in the tank, for measuring an impedance which corresponds to a second liquid height.

Preferably, the end intended to be dipped of each of the measuring rods or electrodes:
- is offset, with respect to the end of the electrodes or rods of the first means (or of the first pair of electrodes), by a value higher than or equal to the first predetermined height,
- or is covered with an insulating coating or an insulating sleeve, along a length higher than or equal to said first height.

Means for feeding the measuring rods of the first impedance measuring means, or the first pair of electrodes, nd/or the measuring rods of the second impedance measuring means, or of the second pair of electrodes, can be provided, for supplying an AC electrical signal having a null mean.

Preferably, feeding means supply a current, the frequency of which is between 1 kHz and 1 MHz.

One end of each of the measuring electrodes or rods can be free. Therefore, upon measuring, it is intended to be in contact with a liquid the height of which is to be measured.

According to an advantageous alternative, means allow for the mechanical hold of this end.

The two rods or electrodes for measuring the impedance of the first liquid height can have a geometry, for example a shape and/or a gap distance between both rods or electrodes, different from, or identical to that of both impedance measuring rods or electrodes of a second liquid height.

A system for continuously measuring a level of a fluid in a tank of a continuous ink jet (CIJ) printer, includes a device as described above, and means for calculating or estimating the fluid height in said tank.

It can further include means for storing at least one parameter for calculating the height of a fluid and/or one or more data for correcting the height calculated to take account of the presence of a wall of the tank, and/or of the configuration, whether free or not, of the ends of the electrodes.

According to another aspect of the invention, an ink tank, for a continuous ink jet (CIJ) printer, includes:
- at least one wall,
- means for introducing ink into said tank and means for discharging ink from said tank,
- a continuous level measuring device or system, according to one of the preceding claims.

The wall can be electrically conducting; in this case, means are provided such that the tank is electrically insulated, for example, it can be connected to the ground by a very high impedance with respect to the impedances measured, or to be measured, by the system (with a ratio of at least 10 between said very high impedance and the impedances measured or to be measured).

Alternatively, the wall can be electrically insulating.

Such a tank can further include means for holding the first impedance measuring means, or the first pair of electrodes, and the second impedance measuring means, the second pair of electrodes, at a minimum distance from said wall at least equal to the gap between the rods or the electrodes.

The invention also relates to a continuous ink jet printer, including:
- a ink circuit including a tank as described above,
- a printing head,
- hydraulic connection means, for bringing, from the ink tank, an ink to be printed to the printing head and sending, to said ink circuit, an ink to be recovered from the printing head,
- electrical connection means for electrically feeding said printing head.

One object of the invention is also to provide a method for measuring a level in a tank of a continuous ink jet (CIJ) printer, implementing a device or system as described above.

One object of the invention is also to provide a method for measuring a level in a tank of a continuous ink jet (CIJ) printer, including:
- measuring the impedance of a first predetermined liquid height, in said tank;
- measuring the impedance of any second height of the same liquid in said tank;
- calculating or estimating said second height based on the 2 measured impedances, in particular on their resistive components.

Measuring the impedance of the first liquid height can be made with a first pair of electrodes connected in series.

Measuring the impedance of the second liquid height can be made with a second pair of electrodes connected in series.

Such a method allows a continuous and linear measurement, independent of the conductivity of the liquid.

In such a method:

first means for measuring the impedance of a first predetermined liquid height, in said tank, can include two measuring rods or electrodes mounted parallel to each other in the tank, each including a measuring end of a conducting material, for measuring an impedance which corresponds to the first predetermined liquid height, and which remains constant for any second height higher than the first height;

second means for measuring the impedance of an any second liquid height, in said tank, can include two measuring rods or electrodes, each of a conducting material, mounted in parallel in the tank, for measuring an impedance which corresponds to a second liquid height.

A method according to the invention may involve:

a first pair of electrodes for measuring the impedance of the first liquid height, being mounted parallel to each other in the tank, each including a measuring end of a conducting material, for measuring an impedance which corresponds to the first predetermined liquid height, and which remains constant for any second height higher than the first height;

second pair of electrodes for measuring the impedance of the second liquid height, each of a conducting material, mounted parallel to each other in the tank, for measuring an impedance which corresponds to a second liquid height.

According to one embodiment, the measuring rods or electrodes are further electrically fed with an AC electrical signal having a null mean.

The measuring rods or electrodes can be electrically fed with a current, the frequency of which is between 1 kHz and 1 MHz.

Preferably, the end of the rods or electrodes is held with holding means.

Further preferably, the rods or electrodes are held at a distance from the wall of the tank at least equal to the gap between the rods or electrodes. In an embodiment, the electrodes are held at a distance from the wall of the tank higher than each of the gaps between the electrodes of each pair of electrodes.

In a method and a device according to the invention, the distance between the rods or electrodes and the walls of the tank is held higher than the gap between the rods or electrodes. The rods or electrodes are for example arranged as a square.

A correction of the height calculated or estimated can be performed, to take account of the presence of a wall of the tank and/or of the configuration, whether free or not, of the ends of the electrodes.

The invention also relates to a computer program comprising instructions to implement a method according to the invention, in particular as described above.

The invention also relates to a data medium, that can be read by a computing system, including the data, in coded form, to implement a method according to the invention, in particular as described above.

The invention also relates to a software product including a program data medium means, likely to be read by a computing system, allowing to implement a method according to the invention, in particular as described above.

BRIEF DESCRIPTION OF THE FIGURES

FIGS. 3A and 3C represent embodiments of a sensor according to the present invention, FIG. 3B represents a wiring diagram of 2 of the electrodes of a sensor according to the present invention, FIGS. 8A-8C represent various configurations of electrodes, with free ends (FIG. 8A), or with end holding means (FIG. 8B), or further, with a separator (FIG. 8C)

DETAILED DISCLOSURE OF ONE EMBODIMENT

Figure 3A:
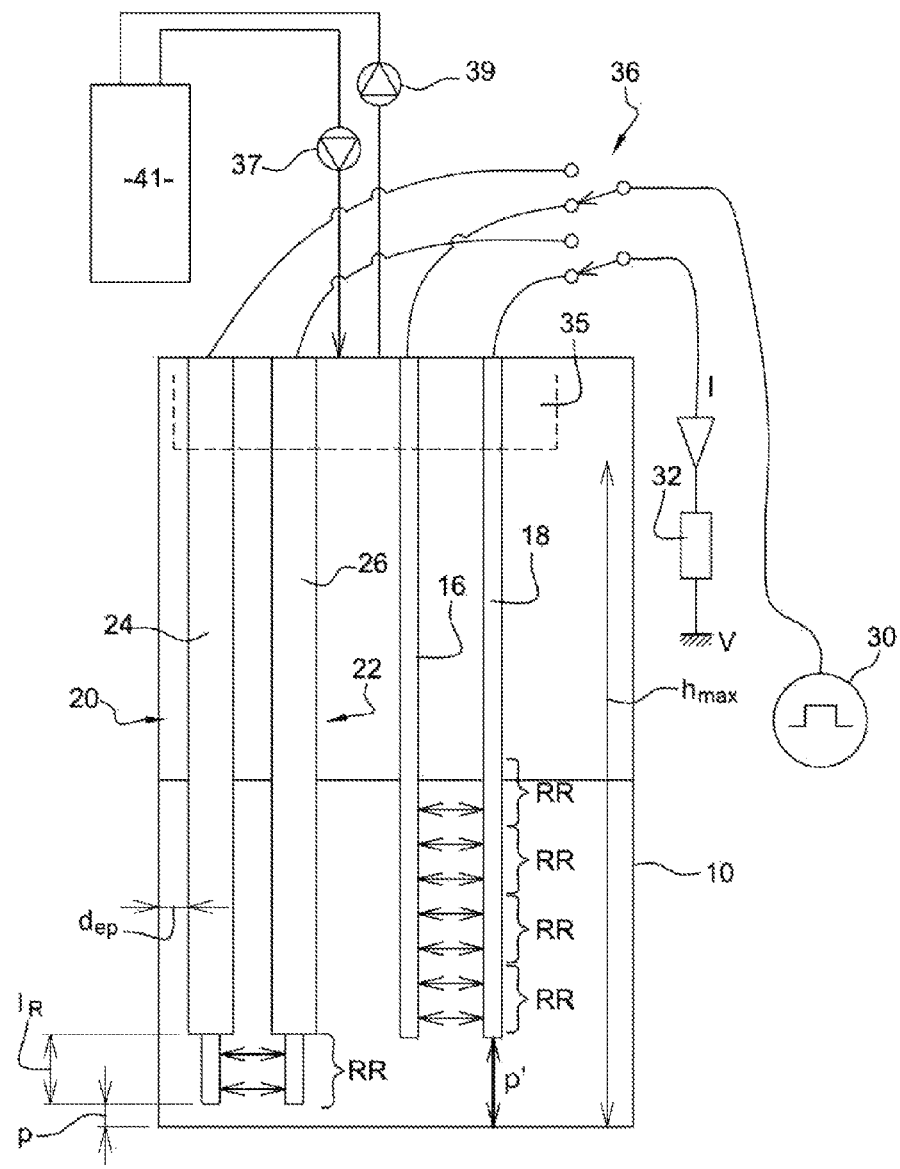

An example of a measuring device according to the invention is illustrated in FIG. 3A.

Herein, it is provided in a tank 10.

It includes 2 conducting rods, or electrodes 16, 18 and 2 reference rods, or electrodes 20, 22.

Preferably, the reference electrodes are identical to each other and/or the measuring electrodes are identical to each other.

Each of the reference rods, or electrodes is covered, on most of its length, with a coating, or a sleeve 24, 26, of a dielectric or electrically insulating material, which only allows an end portion (active part) of the corresponding electrode, having a length $l_R$, to project. Thus, it enables a liquid level (or first height), or a signal corresponding to such a liquid level, to be measured or detected, with a depth $l_R+p$, p being the distance between the free end of the reference electrode and the bottom of the tank 2.

The length $l_R$ is preferably determined by a compromise: it is chosen sufficiently great to achieve a good accuracy and sufficiently low to limit the volume size not measured.

$l_R$ is preferably at least equal to 2 times the diameter (for electrodes having a circular cross-section), or 2 times a side of the cross-section, of the electrodes (not including the coating 24, 26), in order to limit the extent of the non-direct field lines (that is those that are not perpendicular to the electrodes, as illustrated in FIGS. 8A-8B).

Further preferably, $I_R$ is equal to 5 times the diameter of the electrodes 5 times a side of the cross-section.

$I_R$ can be included between one of the above indicated values and 25% (or 10%) of the height of the measuring electrodes.

Each of the measuring rods 16, 18 includes an electrode which is, in turn, not covered with a sleeve, of a dielectric or electrically insulating material, at least on the part which is included between the free end of the electrode, intended to be the closest to the bottom of the tank, and the maximum level $h_{max}$ desired to be measured. The different electrodes are of conducting material, for example of stainless steel. Generally, a device according to the invention enables a second liquid height, included between the minimum level defined by, at least, the first height and a maximum level, to be measured using the electrodes 16, 18, the amplitude between the minimum level and the maximum level being at least 4 to 10 times the first height. Said second height of liquid can be in the lower half of the tank. A level located in said lower half of the tank, above said minimum level, can therefore be measured or detected. The maximum level can be defined by an operator or by the manufacturer of the tank or of the machine incorporating the tank, for example an ink jet printer. It is a level which the liquid level can reach, but which it should not exceed. Reaching the maximum level can trigger a warning signal.

The pairs of electrodes are fed with a current by generator means or a current or voltage generator 30. The electrodes of each pair are electrically arranged in series with an electrical circuit connecting said electrodes in series. Preferably, the current supplied is an AC electric current, having a null mean to avoid any electrolysis. The current frequency is neither too low (once again, to avoid any electrolysis), nor too high (to avoid any capacitive coupling displacement current between the electrodes). For example, the current frequency is between 10 kHz and 50 kHz, and it is for example equal to 15 kHz or 20 kHz or 30 kHz.

In order to more precisely investigate these phenomena, the wiring diagram presented in FIG. 3B of 2 electrodes 16, 18 partially dipped into a tank 10 is considered.

The electric impedance of this system includes several terms: the real (resistive) component and an imaginary (capacitor or self) component. The term "self" has herein no physical sense and can be omitted. On the other hand, the capacitive coupling between the electrodes can generate a non-negligible displacement current relative to the conduction term, for example if the frequency of the measurement signal is too high.

By taking the notations of FIG. 3B, the impedance between 2 partially dipped cylindrical electrodes is written as:

in the liquid:

$$Cl = \frac{\pi \varepsilon_o \varepsilon_r h l}{\text{Log}(D/2r)}$$

in air:

$$Ca = \frac{\pi \varepsilon_o h a}{\text{Log}(D/2r)}$$

The total capacitance C is thus:

$$C = Ca + Cl$$

The total capacitance is the sum of both capacitors in parallel. It appears that this stray capacitance is enhanced, and detrimental, when the tank is full of ink and for liquids having a strong dielectric constant. For water, the relative permittivity is 80, whereas it is only a few units in solvents such as alcohol, MEK, etc.

The capacitive coupling remains negligible if its impedance remains high relative to the electric resistance between electrodes. The electric current flowing between the electrodes being low (preferably small relative to 1 Ampere), for example between 10 μA and 10 mA, the (electrostatic) field lines are coincident with current (electrokinetic) lines; the geometric coupling factors for determining resistance and capacitance are identical and are thus simplified by making the product RC (Zr=Zc).

The capacitive coupling impedance is written as:

$$Zc = \frac{1}{j\omega Cl}$$

The electric resistance impedance is written as:

$$Zr = Ra = \frac{1}{\sigma} \frac{\text{Log}(D/2r)}{ha}$$

The frequency for which the impedances are equivalent is thus written as:

$$f = \frac{\sigma}{2\pi \varepsilon_o \varepsilon_r}$$

The ink conductivity σ is taken equal to 1 000 μS/cm, the vacuum permittivity $\varepsilon_o$ equal to $8.8 \cdot 10^{-12}$ F/m and the water relative permittivity $\varepsilon_r$ equal to 80.

The numerical application gives a cut-off frequency of 22 MHz for a water-based-ink filled tank. In practice, a working frequency lower than 10 Mhz or even 1 MHz or even 100 kHz will be taken.

On the other hand, at the interface of the electrodes and the conducting liquid, the electric current flow is ensured by two mechanisms which are relayed as a function of the interface potential. If the potential drop at the interface remains lower than one volt, the current that flows is a displacement current through the electric double layer. If the interface potential typically exceeds one volt, then the current flow is ensured by an electronic exchange which results in an electrolysis of the liquid. The diffusion of chemical species in the vicinity of the electrode governs the current density at the electrode interface.

For the measure not to depend on chemical species in solution, which offers a formulation freedom, the current at the electrode interface is written as:

$$i = C_{db} V_{db} f$$

where $C_{db}$ is the double layer capacitance:

$$C_{db} = \frac{\varepsilon_o 2\pi r h l}{e}$$

with e=interface thickness defined on an atomic scale. As a first approximation, it is assumed that e=1 Å ($10^{-10}$ m) and where $V_{db}$ is the double layer potential=1 V.

The current i which flows between the electrodes is determined by the Ohm's law:

$$U=Ri$$

where U is the bias voltage of the electrodes and R the electric resistance between electrodes:

$$R = \frac{1}{\sigma}\frac{\mathrm{Log}(D/2r)}{hl}$$

The minimum frequency for which the electrolysis mechanism is not triggered can be determined:

$$f = \frac{U}{RC_{db}V_{db}} \Rightarrow f = \frac{U}{V_{db}}\frac{\sigma e}{2\pi r \varepsilon_o \mathrm{Log}(D/2r)}$$

with: U=5 volts–$V_{db}$=1 volt and D=20 mm–2r=2 mm.

A numerical application gives a minimum operating frequency of 390 Hz. In practice, a minimum frequency of 500 Hz, or even 1 kilohertz can thus be considered.

In view of the results above, a frequency lower than 10 MHz or even 1 MHz or 100 kHz and higher than 500 Hz or 1 kHz can be taken.

Means 32, for example a voltage detector, enable a voltage $V_M$ between both measuring rods to be measured. For example, these means 32 include a resistor which enables both the intensity to be measured by the voltage measurement and the current to be limited in the circuit.

Preferably, these means enabling a measurement to be made perform a sampling on peak values, and then an amplification.

Means 36, such as multiplexing means, typically a multiplexer as used in electronics, can be provided to perform, alternatively, a measurement at the terminals of both measuring rods and a measurement at the terminals of both reference rods. Thus, the pair at the terminals of which no measurement is made is completely disconnected and has no influence on the measurement made at the terminals of the other pair, and any coupling effect of the electrode pairs is avoided. In this configuration, the same voltage measuring means 32 can be used for measuring a voltage $V_M$ between both measuring rods and for measuring a voltage $V_R$ between both reference rods.

For example, a measurement is performed during 100 ms with both measuring rods, and then during 100 ms with both reference rods. The measurement durations with both measuring rods and then both reference rods can be equal, or different: for example, the ratio of the measurement period with both measuring rods to the measurement period with both reference rods can be between 5 and 10.

From the voltage measurement $V_M$ and $V_R$, an impedance, a measurement impedance (or its resistive component) $R_M$ and a reference impedance $R_R$ (or its resistive component) can be deduced respectively.

Then, $R_R/R_M$ is calculated to deduce therefrom the level $h_M$ of the liquid height by the following formula:

$$h_M = K_1 \cdot (R_R/R_M) - K_0$$

Thus, $R_R/R_M$ (the ratio of the resistive components) is preferably calculated to deduce the ink level therefrom. This formula is independent from the liquid conductivity which, as will be seen herein below, is confirmed by experimental measurements. Surprisingly, it has been noticed that the reference resistance, per mm of ink, is different from the measurement resistance, per mm of ink. (The difference probably comes from the non-direct field lines (that is those which are not perpendicular to the electrodes, as illustrated in FIG. 8A-8B), which are not identical for the reference resistance and the measuring resistance, because of structure differences in the bottom of the electrodes).

A correct measurement can be carried out as soon as the reference electrodes are fully dipped (this is in the case in FIG. 3A) and/or the measurement electrodes of a distance p', with respect to the bottom of the tank, equal to p increased by a length corresponding to the active part of the reference electrodes (this is also the case in FIG. 3A). This previous condition results in p'≥p+$I_R$; p' is preferably equal or close to p+$I_R$. Alternatively, as illustrated in FIG. 3C, the ends of the measurement electrodes can be protected by an insulating coating or insulating sleeves 16', 18', having a length equal to or higher than the active part $I_R$ of the reference electrodes (the other elements of FIG. 3C are identical to those of FIG. 3A). According to one embodiment, the upper part of the insulating sleeves 16', 18' substantially corresponds to the lower part of the sleeves of the electrodes 24, 26.

In the opposite case, the formula $h_M = K \cdot (R_R/R_M) - K_0$ is not valid in the bottom of the tank as long as the ends (over the distance $l_R$) of the reference electrodes are not fully dipped (in this case, the measurement and reference impedances are equal, which gives a constant hm value). But, once the reference electrodes are fully dipped, the above formula can then be applied, coefficients $K_0$ and $K_1$ being experimentally determined.

Electronic means can be programmed, for example in the printer controller, to calculate $h_M$ as a function of the $R_R$ and $R_M$ values. Measurement data are transmitted from the ink tank to the controller, which then carries out data processing and calculating the ink or liquid level.

If the ink level thus calculated is lower than a predetermined threshold level, the controller can trigger a tank filling operation. A hydraulic circuit, comprising for example a pump 37, can be used to fill the tank from a bottle or a cartridge 41. A pump 39 can be used to transfer liquid from the tank to the cartridge.

Testing measurements have been made.

The device implemented is very close to that presented in FIG. 3A, with the following particular data:
  volume of the tank 10: 1 l,
  the electrode ends opposite to the free ends are held by a support 35, for example a plastic part (represented as dashed lines in FIG. 3A) and the 4 electrodes are provided at the vertices of a square with sides of length 20 mm,
  the electrode of each of the reference rods 24, 26 is covered, on most of its length, with a coating, or sleeve 24, 26, which only allows a length $I_R$=10 mm to project at its end,
  the distance p between the bottom of the tank and the free end of each of the electrodes is 20 mm.

A side rule (not represented in the figure) has been mounted to a side of the tank 10 for measuring the liquid height. Thanks to 2 pumps 37, 39, the test liquid can be decanted from a bottle 41 to the tank 10 and vice versa.

The measuring chain of the impedance has been checked and calibrated. The part supporting the rods is set to obtain an identical impedance for both pairs of rods, with a liquid height of 5 mm.

Impedance measurements have been made with this device. They consisted in reading out the impedances on the 2 pairs of rods for liquid heights by 5 mm steps. They have been made with a water- and salt-based liquid, with 4 different conductivities, ranging from 410 µS to 1 660 µS: 410 µS, 765 µS, 1 230 µS, 1 660 µS.

2 other series of measurements have been made with a MEK-based pure ink, and then with the same ink being very diluted, of the conductivity 1 110 µS and 260 µS respectively.

Figure 4A:
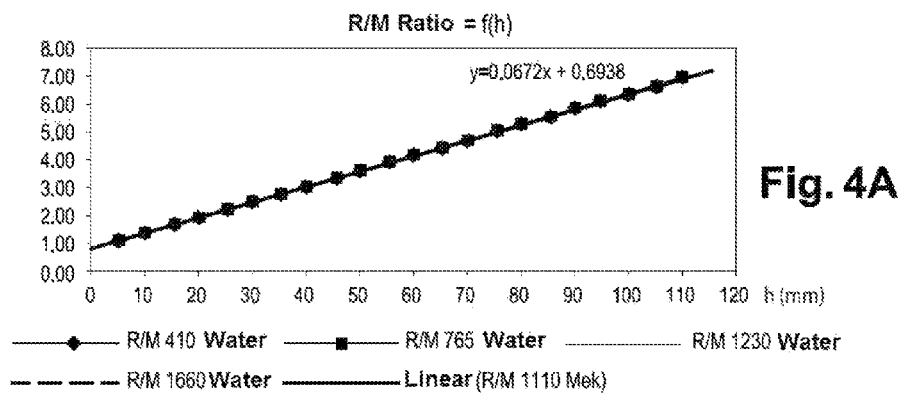
FIGS. 4A and 4B represent results of tests made with a sensor according to the present invention.
Figure 4B:
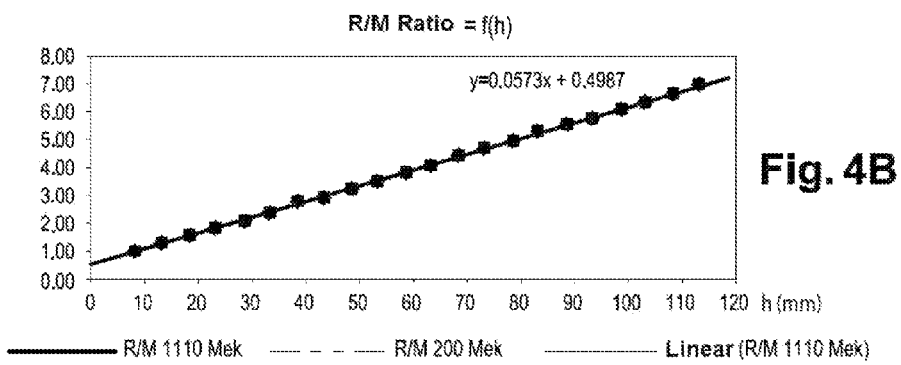

The graphs of FIGS. 4A (water- and salt-based liquid) and 4B (MEK-based ink) represent the RR/RM ratio, between the reference impedance (RR) and the measurement impedance (RM), as a function of the liquid height.

All the read-outs show that the curves at different conductivities are superimposed with each other and are linear.

Generally, the measurements made according to the invention are independent of the conductivity.

In a configuration where the measurement and reference rods are adjusted at the same height (the distance p is the same for the 2 pairs of electrodes), the liquid (ink) height is given by the following relationship:

water-based:

$$H=((RR/RM)*(1/0.0572))-(0.6938/0.0572)$$

$$H=17.48(RR/RM)-12.1$$

MEK-based:

$$H=((RR/RM)*(1/0.0572))-(0.4987/0.0572)$$

$$H=17.48(RR/RM)-8.7$$

The only difference is in the origin offset of the curve, which is explained by the different behaviour of the liquid on the electrodes and the tank wall. More specifically, the surface tension of the liquid is not the same for both inks, which causes a different meniscus.

Generally, the level of an ink having any conductivity, 50 µS to 20 µS, can be measured using a device and a method according to the invention. This is all the more interesting that the conductivity can strongly vary as a function of temperature. For a 50° C. amplitude, the conductivity can be multiplied with a factor 2 or 3. Because of their independence to the conductivity, the measurements made according to the invention are therefore not or hardly altered by temperature variations.

A measuring method and device according to the invention is thus exploitable for measuring a conducting liquid level, in particular of ink or solvent (if it is conducting), in a tank, in particular of a continuous ink jet printer.

Figure 5:
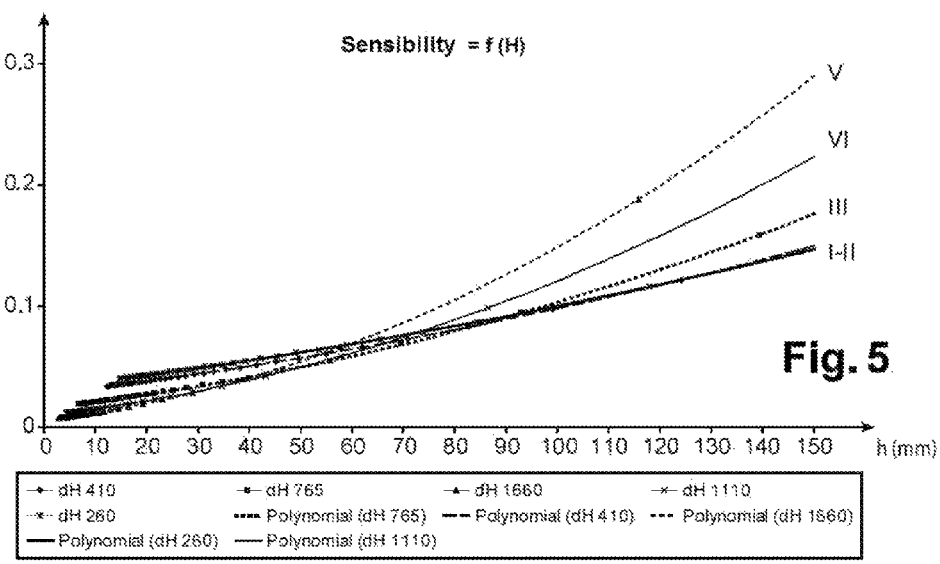
FIG. 5 represents sensitivity curves obtained with a sensor according to the present invention.

FIG. 5 enables to show what the sensitivity of the sensor is, that is the height variation the system allows to measure. The curves which are represented are those of ΔH=f(h), that is, for each conductivity, the change over time of the sensitivity as a function of the height measured. The curves represented relate to:

for curves I-IV: a water- and salt-based liquid, of a conductivity of 410 µS (curve I); 765 µS (curve II); 1660 µS (curve III) respectively;

for curves V-VI: MEK-based pure ink (260 µS (curve IV), then diluted, at 1110 µS (curve V))

It is noticed that the measurement sensitivity decreases with the liquid height, but also with the liquid conductivity. The variation noticed can be further reduced with measuring means having a better performance.

Overall, the sensitivity is lower than 1/10 mm, or 3/10 mm. It can be even better with, once again, measuring means having a better performance.

Figure 6A:
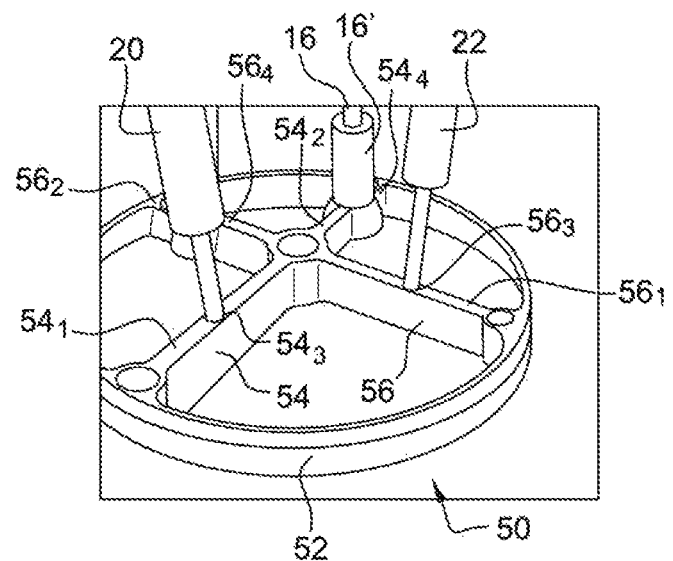
FIGS. 6A, 6B represent embodiments of another structure of a sensor according to the present invention, with a ring for holding the electrodes.
Figure 6B:
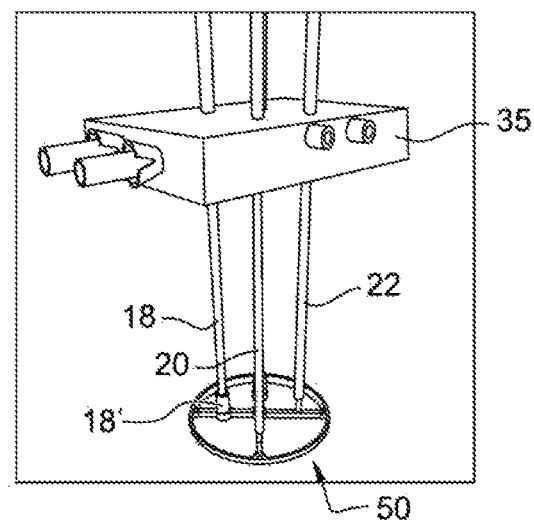

Another embodiment is represented in FIGS. 6A and 6B. The difference with the preceding embodiment is in the presence of means 50 for holding, in an integral manner, the end of the rods or the electrodes. These means 50, also called holder, enable the mechanical stability of the assembly to be enhanced and the gap between the electrodes to be held. These means 50 thus contribute to the measurement stability.

In the embodiment of FIGS. 6A and 6B, these means take the form of a ring 52 which surrounds a cross consisting of 2 diameters 54, 56, or 4 branches (spokes) $54_1$, $54_2$, $56_1$, $56_2$ of the ring. A port $54_3$, $54_4$, $56_3$, (the one on the branch $56_2$ is not visible) on each of the branches of the cross enables the end of the measurement or reference electrode to be accommodated.

In FIG. 6B, the assembly of the electrodes with the means 50 for holding the ends can be seen. The support 35 which holds them at the other end can also be seen.

Impedance measurements were made with this sensor, the electrodes being provided with the means 50, the rest of the system having all the characteristics of that of FIG. 3A. These measurements consisted in reading out the impedances on the 2 pairs of rods every 5 mm. They have been made on a water- and salt-based liquid, with the same 4 conductivities as above, ranging from 410 µS to 1 660 µS.

2 other series of measurements have been made with MEK-based pure ink, and with the same ink being very diluted, respectively of 1 110 µS and 260 µS.

Figure 7A:
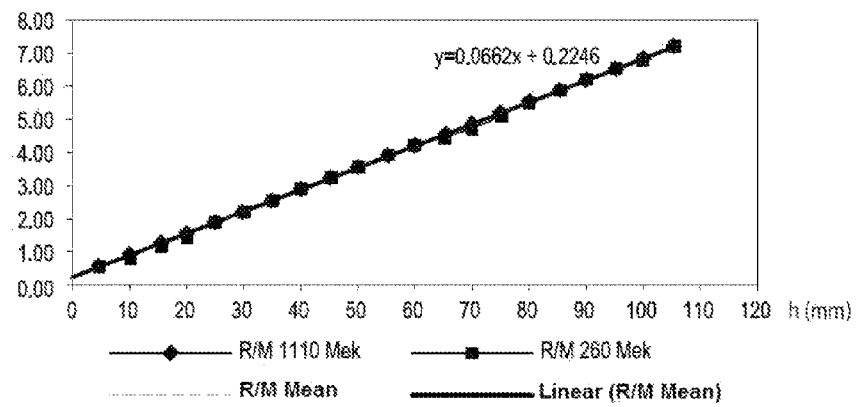
FIGS. 7A, 7B represent results of tests made with a sensor according to the present invention, with a ring for holding the electrodes.

The graphs of FIGS. 7A (MEK-based liquid) and 7B (water and salt based ink) represent the RR/RM ratio, of the reference impedance (RR), or its resistive part or component, to the measurement impedance (RM), or its resistive part or component, as a function of the liquid height.

Figure 7B:
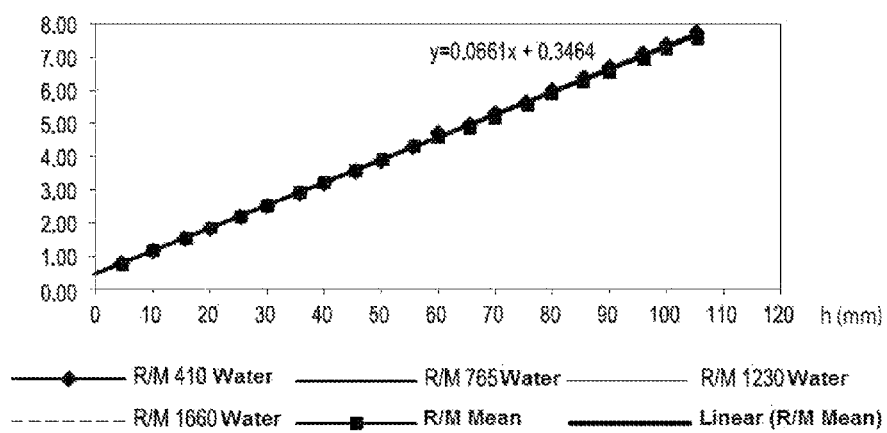

Once again, the read-outs show that the curves at different conductivities (FIG. 7A: 260 µS and 1 110 µS; FIG. 7B: 410 µS, 765 µS, 1230 µS and 1 660 µS) superimposed with each other and are linear. The measurement principle is thus exploitable for measuring a level of conducting liquid in a tank.

In a configuration where the measurement and reference rods are adjusted to the same height (same distance p for the 2 pairs of electrodes), the liquid (ink) height is given by the following relationship:

Water-based:

$$H=((RR/RM)*(1/0.0661))-(0.3464/0.0661)$$

$$H=15.12(RR/RM)-5.24$$

MEK-based:

$$H=((RR/RM)*(1/0.0662))-(0.2248/0.0662)$$

$$H=15.10(RR/RM)-3.39$$

The only difference between both is in the origin offset of the curve, which is explained by the different behaviour (because of the surface tension which is not the same for both liquids, as already explained above) on the electrodes and the tank wall.

It is seen that, for a given configuration (that of FIG. 3A or that of FIGS. 6A and 6B), the proportionality coefficient is the same, substantially close to 17.5 in the case of FIG. 3A, substantially close to 15.1 in the case of FIGS. 6A and 6B.

The proportionality coefficient reflects the influence of the conditions at the bounds (the electrode ends, which may be masked or not) on the field lines distribution, as shown in the schemes of FIGS. 8A-8C.

In FIG. 8A, both reference electrodes 24, 26, the ends of which are free, and the corresponding field lines of the system have been represented.

In FIG. 8B, both these reference electrodes 24, 26 are represented, in the case where their ends are held by a holding part 50.

In FIG. 8C, both these two same reference electrodes 24, 26, the ends of which are embedded in an infinite plate, a separator 60, in the zone defined by the bottom of the sleeves 24, 26 have been represented; this separator 60 avoids the field lines by passing by above. These lines are thus held perpendicular to the conductors of the electrodes.

Impedance measurements have been made with these 3 sensors, the rest of the system having all the characteristics of that of FIG. 3A. These measurements consisted in reading out the impedances on the 2 pairs of rods with a liquid level, by 5 mm steps. They have been made on a water- and salt-based liquid, with a 1 230 μS conductivity.

Figure 9:
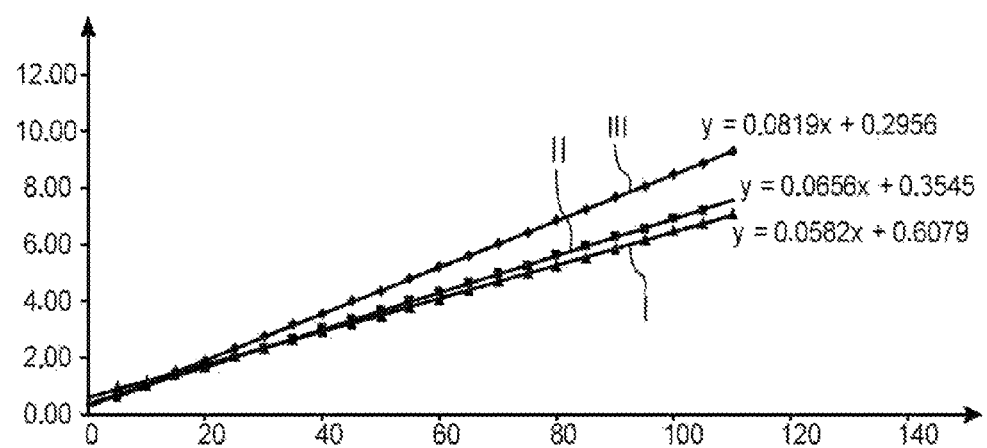
FIG. 9 represents results of tests made with sensor according to the present invention, with various electrode configurations, of the type represented in FIGS. 8A-8C, FIG. 10 schematically represents an electrode structure.

The graphs of FIG. 9 represent the RR/RM ratio, of the reference impedance (RR) to the measurement impedance (RM), as a function of the liquid height (curve I: configuration of FIG. 8A, free ends; curve II: configuration of FIG. 8B, semi-free ends; curve III: configuration of FIG. 8C, masked ends). The liquid height is given by the following relationships:

Rod with free ends (FIG. 8A): $H=((RR/RM)*17.2)+10.4$

Rod with half free ends (FIG. 8B): $H=((RR/RM)*15.2)+5.4$

Rod with masked ends (FIG. 8C): $H=((RR/RM)*12.2)+3.6$

It is noticed that the proportionality coefficient varies according to the configuration; it reflects the influence of the conditions at the bounds on the field line distribution.

Generally, data relating to the proportionality coefficient, as a function of the configuration, and relating to the origin deviation, as a function of ink, can be stored and used upon exploiting the measurements.

Figure 10:
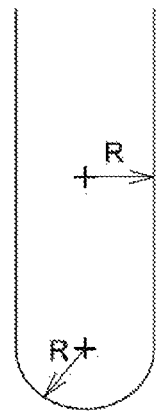

The results obtained could be modelled by considering electrodes at a distance of d=20 mm, each being such as that illustrated in FIG. 10, consisting of a cylinder having a radius R terminated, at its lower end, with a half sphere with a radius R. More precisely, the validity of the following law was able to be shown:

$$h_M = (h_R+B)R_R/R_M - \alpha \cdot B$$

where $B=2R(Ln(d/R)/(1-(R/d)^2))$.

B is a constant which does not depend on the geometry and which models the edge effects: when means enable these edge effects to be decreased, the value of B is modified, to take into account this geometrical modification, using the factor α between 0 and 1: α=0 in the absence of edge effect, α=1 for rounded and free electrode ends, soaked or plunged in a great ink volume.

The results of the preceding figures were able to be compared with values calculated by means of the formula above. It was noticed that the experimental curves have an appearance close to the straight lines from an analytical calculation and that there is further a good quantitative agreement between the case of "free electrode ends" (α=1) as well as for the case "masked electrode ends" (α=0.1).

The formula given above can thus be used for sizing a level measuring system, as well as for calculating the liquid height with the calculating means available in the printer.

Regardless of the embodiment retained, a sensor according to the invention will be set up in a tank 10, such that each electrode is at a distance from any wall of the tank, for example at a minimum distance of at least 20 mm from any wall of the tank. The means 35 for holding the electrodes (FIG. 3A) by their end opposite to that intended to be in contact with the liquid enable this positioning to be made. This precaution enables any influence from the walls on the measurement to be avoided. In the opposite case, it can be attempted to correct measurements by correction data stored beforehand in control means of the printer. These correction data can include at least one further coefficient, or consist in such a coefficient, independent of the conductivity, which enables the advantages of the invention and its linearity to be preserved.

It has been attempted to evaluate the influence of the environment, and in particular the presence of the walls, on the rods.

Figure 11A:
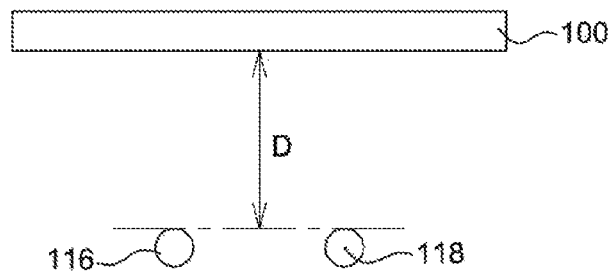
FIGS. 11A-11C represent tests and results of tests in the case of a parallel wall having measuring rods.
Figure 11B:
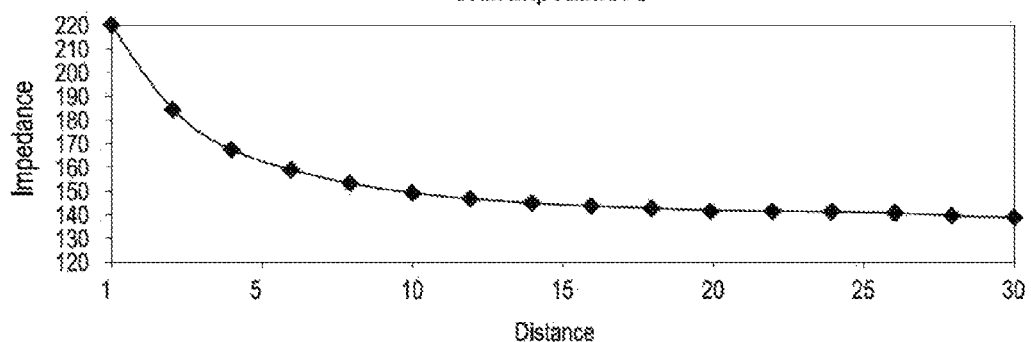
Figure 11C:
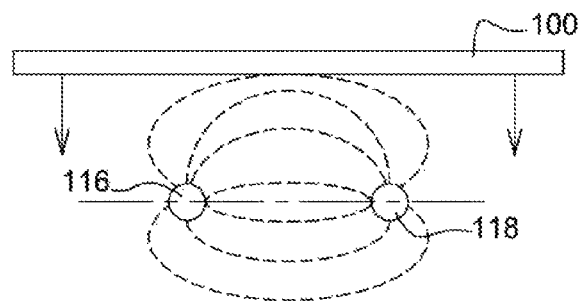

As illustrated in FIG. 11A, measurements have first been made which consist in reading out the impedance between 2 rods 116, 118, which define a plane parallel to an insulating wall 100, as a function of the distance D between each of the rods and this wall. The rods are dipped in 50 mm of a liquid having a conductivity of 1 230 μS. The rods used are without struts (as 50, 60, see FIG. 8C) at the end to be able to reduce D and come into contact with the wall. The results are presented in FIG. 11B. It is seen that the wall has a strong influence on the impedance, mostly when the rods are very close to the wall. This is explained by the fact that, as illustrated in FIG. 11C, most of the conduction lines pass on either side of the axis of the rods. By removing these lines, the impedance is strongly increased when the wall moves closer to the rods.

It has also been attempted to evaluate the influence of a wall perpendicular to the rods (these define a plane perpendicular to the wall).

Figure 12A:
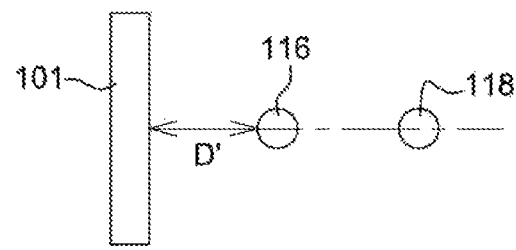
FIGS. 12A-12C represent tests and results of tests in the case of a wall perpendicular to measuring rods.

As illustrated in FIG. 12A, measurements have first been made, which consist in reading out the impedance between 2 rods 116, 118, parallel to each other, but arranged in a plane perpendicular to an insulating wall 101, as a function of the distance D' between the rod 116 being the closest to the wall and this latter. The rods are dipped into 50 mm of a liquid having a conductivity of 1 230 μS. The rods used are without struts (such as 50, 60) at the end to be able to reduce D' and go into contact with the wall.

Figure 12B:
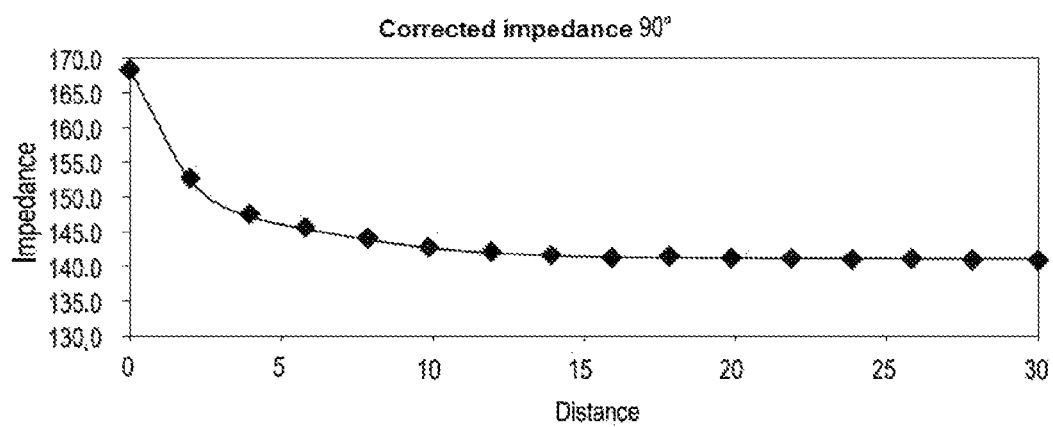

The results are presented in FIG. 12B.

Figure 12C:
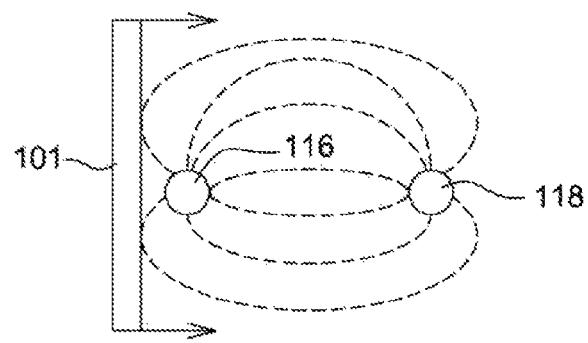

It is seen that the wall has an influence on the impedance, mostly when the rods are very close to the wall. This is explained by the fact that, as illustrated in FIG. 12C, part of the conduction lines pass through behind the rod. It is seen that the influence is lesser that in the previous case, because the conduction paths are longer and thus have a lower influence on the total impedance.

It has also been attempted to evaluate the influence of the walls on the measurement of liquid level.

The measurements herein consisted in drawing the ratio of the reference impedance to the measurement impedance as a function of the liquid height (for a liquid having a conductivity of 1 230 μS).

Figure 13A:
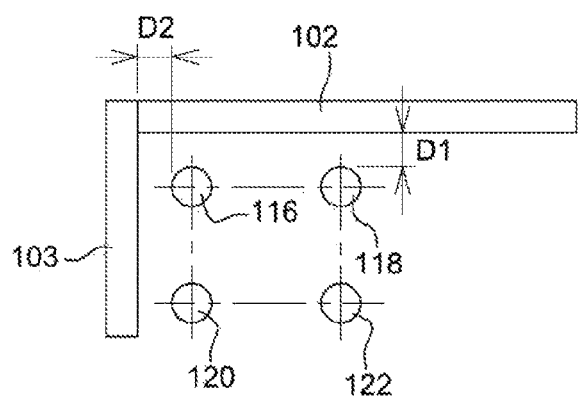
FIGS. 13A-13B represent tests and results of tests for evaluating the influence of the walls on the level measurement.

As illustrated in FIG. 13A, the 2 measuring rods 116, 118 are placed:

in parallel to the wall 102, at a distance D1 from the same, which corresponds to an influence of 50% (in parallel position)

and perpendicular to the wall 103, at a distance D2 from the same (D2 is indeed the distance between the rod 116 closest to the wall 103 and the latter) which corresponds to an influence of 50% in a perpendicular position. The rods 120, 122 are provided in a plane parallel to the rods 116, 118.

One of the reference rods 120, 122 is also in perpendicular influence in order to keep the square arrangement of the rods.

D1 #3 mm and D2 #3 mm are taken.

The reference rods 120, 122 are naked on 10 mm and lowered by 10 mm with respect to the measuring rods according to the geometry given by the part 50 (FIG. 6A).

Figure 13B:
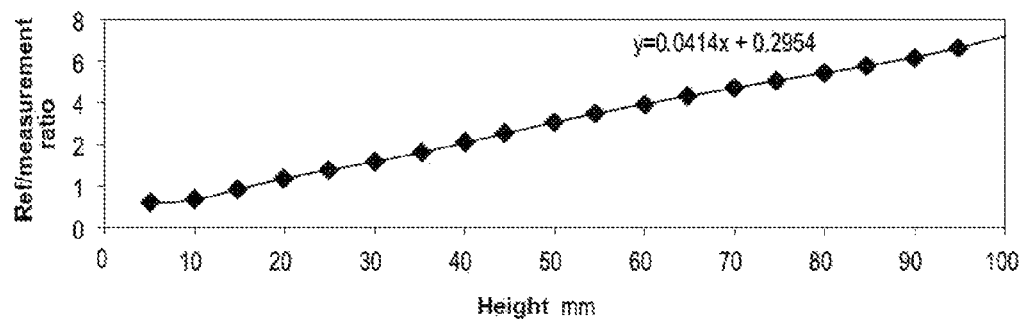

The results are presented in FIG. 13B.

It is noticed that the proximity of the walls parallel to the rods does not question the measuring system and mostly its linearity. On the other hand, the slope which enables the impedance ratio to the height to be connected varies. In our case:

$$H=(24.15*Ratio)-3.38.$$

For the same rods, without wall, there was:

$$H=(17.5*Ratio)-12$$

Since some tanks have a shape at least partly conical, it has also been attempted to evaluate the influence of this configuration type on the measurement of liquid level.

The measurements here consisted in drawing the ratio of reference impedance to measurement impedance as a function of the liquid height.

Figures 14A, 14B:
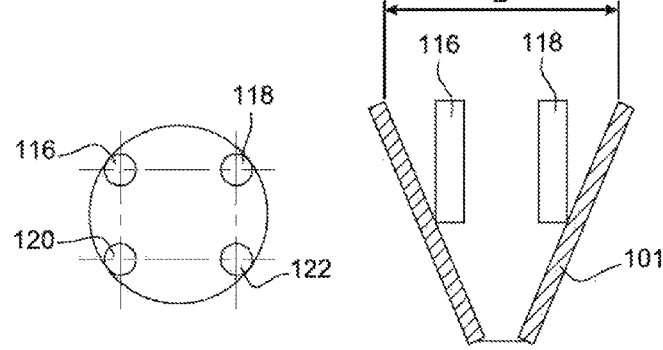
FIGS. 14A-14D represent tests and results of tests for evaluating the influence of a conical-shaped tank wall on the level measurement.
Figure 14C:
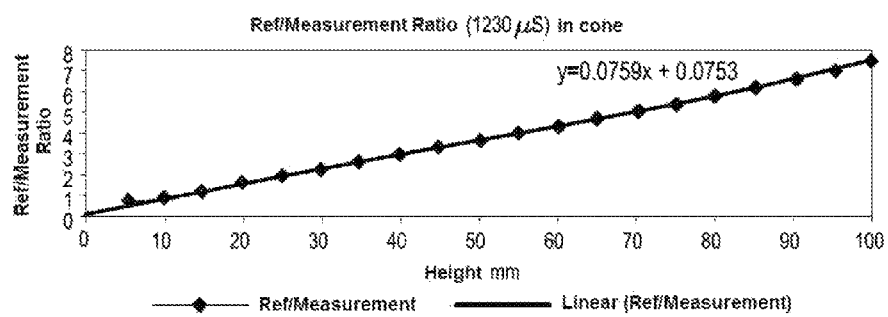

As illustrated in FIGS. 14A (top view) and 14B (side view), the measuring rods 116, 118 are placed in a truncated cone 107 having an angle 22° and a height 150 mm (D being the cone diameter, D=20 mm at the bottom of the cone, D=77 mm at the top thereof). The electrodes are arranged as a square and their ends are in contact with the cone, as seen in FIG. 14B, which corresponds to an extreme embodiment. The results are presented in FIG. 14C (for a liquid of a conductivity of 1 230 µS).

It is noticed that the cone generates a non-linearity on the first 10 or 15 millimeters. This deformation is slight and only comes from the measuring rods 116, 118, which are more influenced by the proximity of the wall.

Figure 14D:
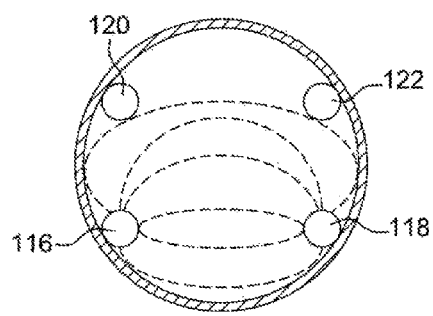

The reference rods 120, 122 only influence the slope, which enables the impedance ratio to be related to the height. A coefficient of 17.5, in a free medium (see the relationship above, H=(17.5*Ratio)−12), has switched to a coefficient of 13.2, in the cone. This decrease comes from the increase in the reference impedance. As illustrated in FIG. 14D, this is explained by the removal of conduction lines on the edge but also from below. In the case of the free rod, the reference impedance, read out during the measurements, switches from 476 Ohms to 624 Ohms in the cone. Besides, the same ratio is found: (476/624)*17.5=13.3.

From these tests, it can be concluded that the properties of the invention are preserved, except for the bottom of the cone (linearity). It will thus be attempted, preferably, to respect a minimum distance, for example of about 15 mm, between the electrodes and the tank wall.

It has been seen that, in all the tests, the reference impedance is a constant which is used for compensating for the variations in the fluid conductivity.

It has also been attempted to know whether the geometry (understood as the shape of the rods and their relative gap) of the reference rods has to be identical to those of the measuring rods. The impedance between 2 rods depends on the conductivity; the question is whether it varies in the same way for two pairs of rods having different shapes and/or gap distances. The tests reported below show that this is not the case.

Measurements have been carried out with a geometry of the reference rods different than that of the measuring rods: the reference rods have here a planar surface, whereas the measuring rods are cylindrical, and the gap between the reference rods is different from the one between the measuring rods. Under these conditions, the reference impedance/measuring impedance ratio has been drawn for 2 different conductivities.

Figure 15:
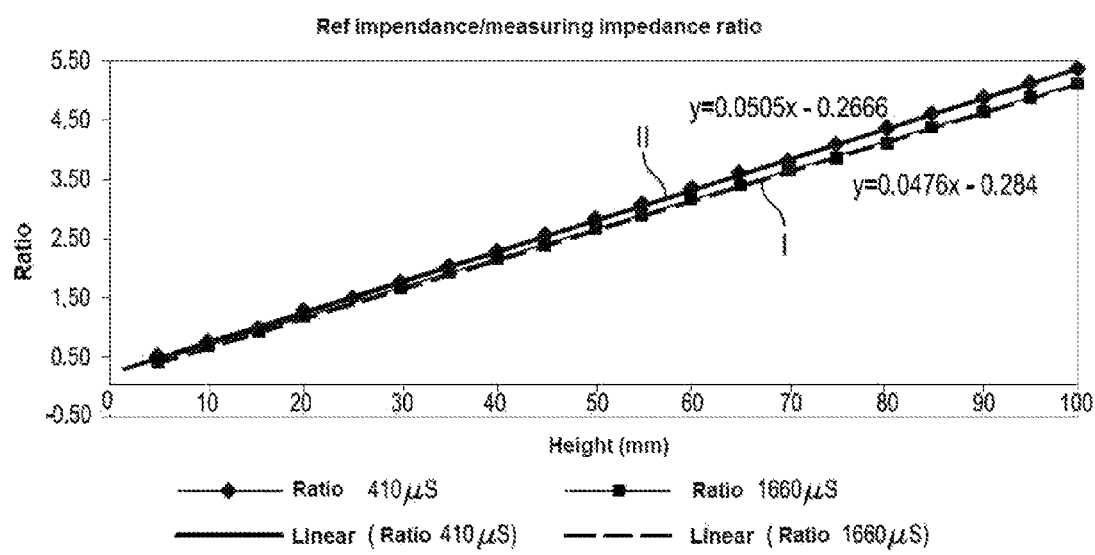
FIG. 15 represents results of tests for evaluating the influence of the geometry of the rods on the level measurement, FIG. 16 schematically represents an assembly including an ink circuit, a controller and user interface means.

The results are presented in FIG. 15 (curve I: conductivity of 410 µS; and curve II: conductivity of 1 660 µS).

It is seen that, for the 2 conductivities, there are reference impedance/measurement impedance slopes slightly different:

$$H=19.8*Ratio+3.75 (curve\ II)\ and$$

$$H=21*Ratio+3.52 (curve\ I).$$

Thus there is a difference, but it is only 5%.

It will be attempted, preferably, to have the same geometry on the 2 pairs of rods to avoid creating a decrease in the measurement accuracy of the height. An identical geometry when it is possible simplifies the design of a system independent of the conductivity.

The above tests show that the proximity of the rods and the tank walls modifies the function which relates the impedance ratio to the liquid height. The influence is more significant for a wall parallel to the pair of rods considered than for a perpendicular wall.

If the reference rods measure a conductivity image and the measuring rods have a geometry, with respect to the walls, which is constant in the height, a linear system is kept. On the other hand, the parameters which enable the height to be calculated can be made dependent on the distance between electrodes and wall.

It can be considered that the influence of the walls becomes negligible as soon as the rods—wall distance is higher than the gap of the rods.

Finally, to reduce as much as possible errors related to the geometries and environment on the accuracy of the liquid height measurements by resistive rods, it is preferred to take symmetric rod geometries, that is the pairs of electrodes have an identical geometry: the distance between the 2 measuring electrodes is the same as that between the 2 reference electrodes and the shape of the 2 measuring electrodes is the same as that of the reference electrodes; it is also preferred, for the same reason, to take a distance between electrodes and walls of the tank as high as possible; preferably, a rods—wall distance is selected higher than the gap of the rods.

An ink circuit of an ink jet printer can include an ink tank provided with means for measuring an ink level according to the present invention. An example of an ink circuit is described for example in document WO 2011/076810.

It is reminded that the ink circuit mainly provides the following functions:
  supplying ink of a suitable quality under pressure to the drop generator of the head 1,
  recovering and recycling unused fluids for printing back from the getter of the head 1,
  sucking in for draining the drop generator located in the head 1,
  supplying solvent to the head 1 for rinsing performed during head maintenance operations.

Figure 1:
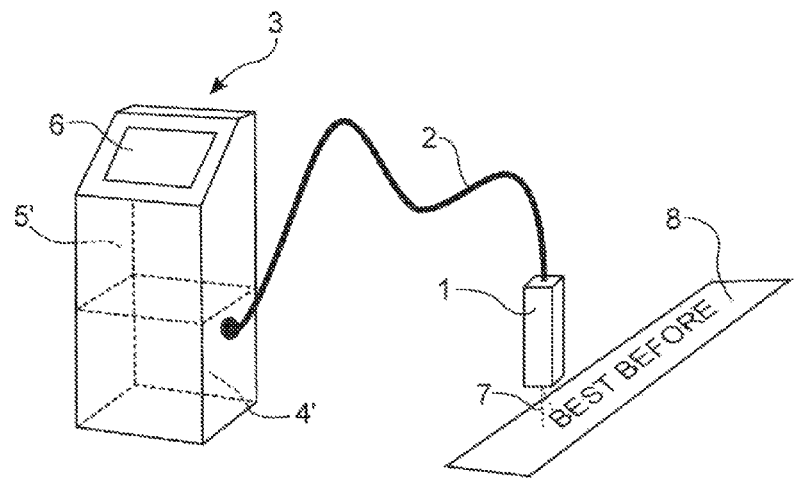
FIG. 1 represents a known printer structure.

A hydraulic circuit, comprising for example one or more conduits or ducts and a pump, can be used to send ink and/or solvent from a tank according to the invention to a printing head 1 (see FIG. 1) of an ink jet printer.

Figure 16:
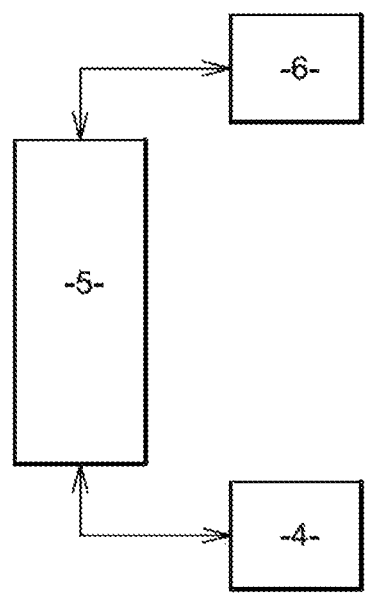

A system including an ink circuit 4, including a tank provided with a measuring device as described above, and means for storing and processing the data measured is illustrated in FIG. 16.

The ink circuit 4 sends information, in particular fluid height data in a tank, measured with a sensor according to the invention, to the controller means 5. These means enable the printer to be driven. A use interface 6 can be provided to allow the interaction of an operator with the printer.

The means 5 can be programmed to:

process data measured by a sensor according to the invention. In particular, the data relating to the impedance of a first predetermined height of the liquid, in said tank, and the data relating to the impedance of a second height of the liquid in said tank, are processed to calculate or estimate the resistive components of the 2 impedances measured, independently of the liquid conductivity, and then the second height is calculated or estimated based on said the resistive components;—
send an instruction for filling the tank, for example from a reservoir ink bottle 41 (FIG. 3A), depending on the result of the liquid height calculation. If this result gives a value lower than a pre-set threshold value, the filling is automatically triggered.

The body, or printer console 3 (FIG. 1) mostly contains the ink circuit 4, the controller 5 for driving the printer and a user interface 6 to allow interaction with the printer.

The controller 5 can for example include a micro-computer or a micro-processor and/or one (or more) electronic board(s) and/or one (or more) electrical circuit(s) or electronic circuit(s) and/or an on-board software, the programming of which provide(s) for driving the ink circuit 4 and the printing head 1. This controller enables printing instructions to be transmitted to the head but also motors and valves of the system to be driven in order to manage the ink and/or solvent supply of the circuit as well as the recovery of the ink/air mixture from the head. It is thus programmed for that purpose.

The means 5 can further include means for storing at least one datum of fluid height calculation parameters (for example one or more of the formulae above) and/or one or more correcting data, for example to take account of the presence or the distance of a tank wall and/or the configuration, whether free or not, of the ends of the electrodes.

Instructions to implement a method according to the invention, in particular as described above, can possibly be embodied as a computer program.

The means 5 can include means for reading a data medium, including the data, encoded from, to implement a method according to the invention, in particular such as described above.

Alternatively, a software product includes a program data medium means, likely to be read by a computing system 5, enabling a method according to the invention, in particular such as described above, to be implemented.

Figure 2:
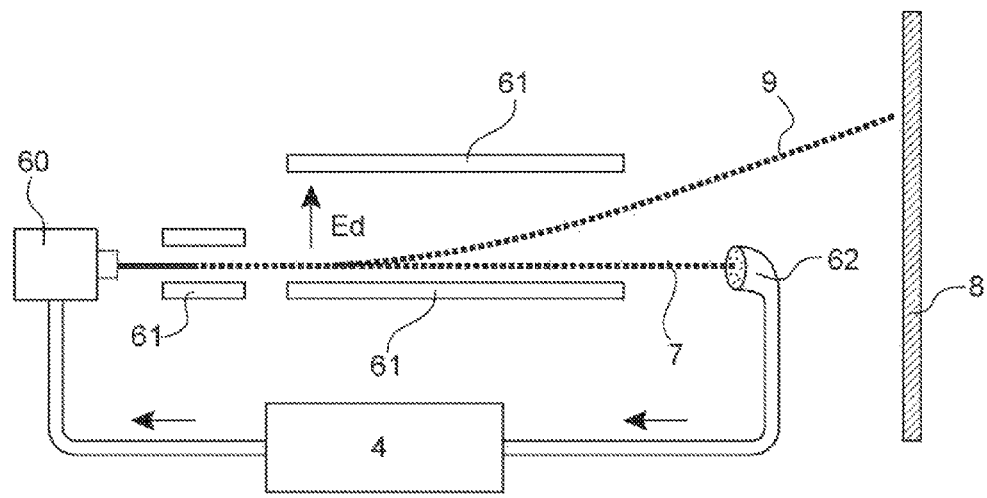
FIG. 2 represents a known structure of a printing head of a CIJ type printer.

The invention can be implemented in a continuous ink jet (CIJ) printer as the one described above in connection with FIGS. 1 and 2. This includes in particular a printing head 1, generally offset from the body of the printer 3, and connected thereto by means, for example in the form of a flexible umbilical 2 joining the hydraulic and electrical connections for the head to be operated.

The invention claimed is:

1. A device for measuring a level of an ink in a tank of a continuous ink-jet printer, including:
   a first pair of electrodes and a circuit for connecting this pair of electrodes in series, for measuring an impedance of a first predetermined height of the ink, in said tank,
   a second pair of electrodes and a circuit for connecting this second pair of electrodes in series, wherein the second pair of electrodes is to be energized independently of the first pair of electrodes by the circuit for measuring an impedance of a second height of the ink in said tank, this second height being included between said first height and a maximum level;
   a controller that controls delivery of an alternating current having a frequency of at least 500 Hz to the first and second pairs of electrodes to energize said electrodes, and calculates said second height, from the resistive components of the 2 impedances measured, independently of the ink conductivity.

2. The device according to claim 1, further including a multiplexer allowing multiplexed measurements using the first pair of electrodes and the second pair of electrodes.

3. The device according to claim 1, the first pair of electrodes being intended to be mounted in parallel in the tank, each including a first measuring ends of a conducting material, for measuring the impedance which corresponds to the first predetermined liquid height, and which remains constant for any second height higher than the first height.

4. The device according to claim 3, the electrodes of the second pair of electrodes being of a conducting material, and intended to be mounted in parallel in the tank, for measuring an impedance which corresponds to the second liquid height.

5. The device according to claim 4, the end intended to be dipped of each electrode of the second pair of electrodes:
   being offset, with respect to the end of the first pair of electrodes, by a value higher than or equal to the first predetermined height,
   or being covered with an insulating coating or an insulating sleeve, along a length higher than or equal to said first height.

6. The device according to claim 1, further including at least one of:
   an electrical supply for supplying the electrodes of the first pair of electrodes and/or the electrodes of the second pair of electrodes with an AC electrical signal having a null mean;
   a current supply to the first pair of electrodes and/or the second pair of electrodes, the frequency of which is between 1 kHz and 1 MHz.

7. The device according to claim 1, further including a holder mechanically holding one end, intended to be in contact with a liquid to be measured in said tank, of the electrodes of the first pair of electrodes and/or of the electrodes of the second pair of electrodes.

8. The device according to claim 1, both electrodes of the first pair of electrodes having a geometry defining a shape and/or a gap distance between both electrodes, different from, or identical to, a respective shape and/or a gap distance defined by both electrodes of the second pair of electrodes.

9. The device according to claim 1, further including means for storing at least one parameter for calculating said second height of a fluid and/or one or more data for correcting the second height calculated to take account of the presence of a wall of the tank, and/or of the configuration, whether free or not, of the measuring ends of the electrodes.

10. A tank for a continuous ink jet (CIJ) printer, including:
at least one wall,
at least one hydraulic circuit (37, 38) for introducing ink and/or solvent into said tank and for discharging ink and/or solvent from said tank,
a level measuring device, according to claim 1.

11. The tank according to claim 10, wherein:
the first pair of electrodes are intended to be mounted in parallel in the tank, each including a measuring end of a conducting material, for measuring an impedance which corresponds to the first predetermined liquid height, and which remains constant for any second height higher than the first height,
the electrodes of the second pair of electrodes are of a conducting material and are intended to be mounted in parallel in the tank, for measuring an impedance which corresponds to a second liquid height,
a holder being for maintaining the electrodes at a distance from said wall, said distance being larger than each of the gaps between the electrodes of each pair of electrodes.

12. A continuous ink jet printer, including:
a ink and/or solvent circuit including a tank according to claim 10,
a printing head,
a hydraulic circuit, for bringing, from the tank, a liquid to be used by the printing head and, if the liquid is ink, a hydraulic circuit for sending, to said tank circuit, an ink to be recovered from the printing head,
electrical connections for electrically feeding said printing head.

13. The device according to claim 1, wherein:
each electrode included in the first pair of electrodes comprises a first measuring end, and the first pair of electrodes is configured to extend in a depthwise direction into the tank to position the first measuring ends at a first depth in the tank for measuring the impedance of the first predetermined height of the ink, and
each electrode in the second pair of electrodes comprises a second measuring end, and the second pair of electrodes is configured to extend in the depthwise direction into the tank to position the second measuring ends at a second depth in the tank, that is different from the first depth, for measuring the impedance of a second height of the ink in said tank.

14. A method for measuring a level of a liquid including ink and/or solvent in a tank of a continuous ink jet (CIJ) printer, including:
with a first pair of electrodes and a circuit for connecting the first pair of electrodes in series energizing the first pair of electrodes with an alternating current having a frequency of at least 500 Hz to measure the impedance of a first predetermined liquid height, in said tank;
with a second pair of electrodes and a circuit for connecting the second pair of electrodes in series, wherein the second pair of electrodes is energizable independently of the first pair of electrodes by the circuit energizing the second pair of electrodes with an alternating current having a frequency of at least 500 Hz to measure the impedance of a second height, of the same liquid in said tank, this second height being any height included between said first height and a maximum height; and
calculating said second height as a function of the resistive components of the 2 impedances measured.

15. The method according to the claim 14, wherein:
measuring the impedance of the first liquid height is made with a first pair of electrodes connected in series,
measuring the impedance of the second liquid height is made with a second pair of electrodes connected in series.

16. The method according to claim 15, wherein:
the first pair of electrodes, mounted parallel to each other in the tank, each electrode of said first pair of electrodes including a measuring end of a conducting material, said first pair of electrodes measuring an impedance which corresponds to the first predetermined liquid height and which remains constant for any second height higher than the first height;
the second pair of electrodes, each electrode of said second pair of electrodes being made of a conducting material, mounted parallel to each other in the tank, for measuring an impedance which corresponds to a second liquid height.

17. The method according to claim 16, further comprising at least one of:
electrically feeding at least the second pair of electrodes electrically with an AC electrical signal having a null mean;
electrically feeding at least the second pair of electrodes with a current, the frequency of which is between 1 kHz and 1 MHz.

18. The method according to claim 15, further comprising at least one of:
holding the end of the electrodes with a holder;
holding the electrodes at a distance from the wall of the tank higher than each gap between the electrodes of each pair of electrodes.

19. The method according to claim 15, wherein the distance between the electrodes and the walls of the tank is held higher than the gap between the electrodes.

20. The method according to claim 15, further including correcting the second height calculated to take account of the presence of a wall of the tank and/or of the configuration, whether free or not, of the ends of the electrodes.

21. A device for measuring a level of an ink in a tank of a continuous ink-jet (CIJ) printer, including:
a first pair of electrodes and means for connecting this pair of electrodes in series, for measuring an impedance of a first predetermined height of the ink, in said tank,
a second pair of electrodes and means for connecting this second pair of electrodes in series, to be energized independently of the first pair of electrodes by the circuit for measuring an impedance of a second height of the ink in said tank, this second height being included between said first height and a maximum level;
a controller that controls delivery of an alternating current having a frequency of at least 500 Hz to the first and second pairs of electrodes to energize said electrodes, and calculates said second height, from the resistive components of the 2 impedances measured, independently of the ink conductivity.

22. The device according to claim 21, wherein:
each electrode included in the first pair of electrodes comprises a first measuring end, and the first pair of electrodes is configured to extend in a depthwise direction into the tank to position the first measuring ends at a first depth in the tank for measuring the impedance of the first predetermined height of the ink, and
each electrode in the second pair of electrodes comprises a second measuring end, and the second pair of electrodes is configured to extend in the depthwise direction into the tank to position the second measuring ends at a second depth in the tank, that is different from the first depth, for measuring the impedance of a second height of the ink in said tank.

* * * * *

UNITED STATES PATENT AND TRADEMARK OFFICE
CERTIFICATE OF CORRECTION

PATENT NO. : 9,701,128 B2  
APPLICATION NO. : 14/919156  
DATED : July 11, 2017  
INVENTOR(S) : Jean-Pierre Arpin Page 1 of 1

It is certified that error appears in the above-identified patent and that said Letters Patent is hereby corrected as shown below:

In the Specification

Column 10, Line 26, "$h_M=K \cdot (R_R/R_M)-K_0$" should read --$h_M=K_1 \cdot (R_R/R_M)-K_0$--

Column 11, Line 37, "20 µS" should read --20k µS--

Signed and Sealed this  
Fifth Day of December, 2017

Joseph Matal  
*Performing the Functions and Duties of the*  
*Under Secretary of Commerce for Intellectual Property and*  
*Director of the United States Patent and Trademark Office*